(12) United States Patent  (10) Patent No.: US 7,832,181 B2
Schroeder et al.  (45) Date of Patent: Nov. 16, 2010

(54) DETECTION SYSTEM

(75) Inventors: Daniel D. Schroeder, Stacy, MN (US);
Jeremy D. Braun, Northfield, MN (US)

(73) Assignee: Delkor Systems, Inc., Circle Pines, MN (US)

( * ) Notice: Subject to any disclaimer, the term of this patent is extended or adjusted under 35 U.S.C. 154(b) by 153 days.

(21) Appl. No.: 12/266,949

(22) Filed: Nov. 7, 2008

(65) Prior Publication Data

US 2010/0115887 A1 May 13, 2010

(51) Int. Cl.
*B65B 57/02* (2006.01)
(52) U.S. Cl. ............................. 53/53; 53/505; 209/657; 348/92; 356/239.4; 356/240.1; 382/143; 702/35; 702/40
(58) Field of Classification Search ................ 53/53, 53/505, 75, 76; 73/52; 209/529, 656, 657; 348/92, 127; 356/239.4, 239.7, 240.1; 382/143; 702/35, 40; *B65B 57/02, 57/04*
See application file for complete search history.

(56) References Cited

U.S. PATENT DOCUMENTS

| 4,759,074 | A | * | 7/1988 | Iadipaolo et al. ............ 382/152 |
| 4,872,300 | A | | 10/1989 | Luke |
| 4,972,494 | A | | 11/1990 | White et al. |
| 5,095,204 | A | * | 3/1992 | Novini .................... 356/239.4 |
| 5,363,968 | A | | 11/1994 | Soloman |
| 5,515,159 | A | | 5/1996 | Sites et al. |
| 5,943,436 | A | * | 8/1999 | Ebel et al. .................... 382/143 |
| 6,384,421 | B1 | * | 5/2002 | Gochar, Jr. .................... 702/40 |
| 6,401,936 | B1 | | 6/2002 | Isaacs et al. |
| 6,732,013 | B2 | * | 5/2004 | Alberts ....................... 700/226 |
| 7,209,575 | B2 | * | 4/2007 | Spaeth .................... 356/239.4 |
| 2001/0016059 | A1 | * | 8/2001 | Krahn et al. ................. 382/141 |
| 2005/0050451 | A1 | * | 3/2005 | Abdollahi et al. ........... 715/502 |
| 2007/0296963 | A1 | | 12/2007 | Parker et al. |

FOREIGN PATENT DOCUMENTS

| JP | 2005009981 A | * | 1/2005 |
| JP | 2005037328 A | * | 2/2005 |
| JP | 2005083877 A | * | 3/2005 |

(Continued)

OTHER PUBLICATIONS

Machine translation of JP 2005009981 A, retrieved from JPO website, Jun. 4, 2010.*

(Continued)

*Primary Examiner*—Stephen F Gerrity
(74) *Attorney, Agent, or Firm*—Vidas, Arrett & Steinkraus

(57) ABSTRACT

A foil lid inspection system for detecting and separating defective foil lids on a container in a production line includes one or more light sources, an inspection camera, and inspection software. The light sources are positioned to direct light in an upward direction to illuminate the container. The inspection camera is positioned above the foil lid, and the camera includes one or more outputs. The inspection software is in communication with the inspection camera. The inspection software is constructed and arranged to determine if the foil lid on the container is defective. A reject signal is applied to an output if the software determines that the foil lid is defective.

7 Claims, 11 Drawing Sheets

FOREIGN PATENT DOCUMENTS

JP    2005153982 A  *  6/2005
JP    2006266690 A  *  10/2006

OTHER PUBLICATIONS

Machine translation of JP 2005037328 A, retrieved from JPO website, Jun. 4, 2010.*

Machine translation of JP 2005083877 A, retrieved from JPO website, Jun. 4, 2010.*

Machine translation of JP 2005153982 A, retrieved from JPO website, Jun. 4, 2010.*

Multi-Functional Inspection System, KRONES Checkmat Label Inspector, printed Aug. 2005.

* cited by examiner

DETECTION SYSTEM

CROSS-REFERENCE TO RELATED APPLICATIONS

Not Applicable

STATEMENT REGARDING FEDERALLY SPONSORED RESEARCH

Not Applicable

FIELD OF THE INVENTION

The present invention is directed generally to a lid detector used in a conveyor system, and in particular to an in-line lid detector that detects torn or misaligned foil lids in a production line having a high speed controlled diverting gate for redirection of failed product.

BACKGROUND OF THE INVENTION

Product inspection is critical to any manufacturing operation. This is especially true when it comes to the manufacture of food products, and no more acutely so than with respect to products that contain dairy. While it is important for obvious health reasons to ensure that the containers holding dairy-based products are properly sealed at the factory, manufacturers recognize that an improperly sealed container can wreck havoc if that container were to spill in a production line. The production line would most likely need to be shut down temporarily while any affected machines are cleaned to remove the spilled product. At best, such a shut down results in product delays, and at worst, if a line was scheduled to run at full capacity, such a shut down means a permanent loss of revenue.

In many prior art inspection systems, product that is rejected as being defective for any reason is ejected from the conveyor system through a diverting mechanism while good product is allowed to continue along the conveyor system to the next stage. An example of which is described in U.S. Pat. No. 4,872,300, the entire contents of which is incorporated herein by reference.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention, a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided for the purposes of complying with 37 C.F.R. §1.72.

BRIEF SUMMARY OF THE INVENTION

In at least one embodiment, the invention is directed to a foil lid inspection system for detecting and separating defective foil lids on a container in a production line. The system comprises at least one light source for illuminating the container, the at least one light source positioned to direct light in an upward direction at the container. The system further comprises an inspection camera disposed above the foil lid, the camera comprising at least one output. The system further comprises inspection software in communication with the inspection camera, the inspection software being constructed and arranged to determine if the foil lid on the container is defective, wherein a reject signal is applied to the at least one output if the software determines that the foil lid is defective.

In some embodiments, the inspection system is in combination with a controlled divert gate. The gate comprises a plurality of fingers, a plurality of cylinders, and a plurality of pneumatic solenoids. Each of the plurality of fingers is engaged to a cylinder, and each cylinder is in communication with a solenoid, and each solenoid is in electrical communication with an output of a programmable logic controller.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
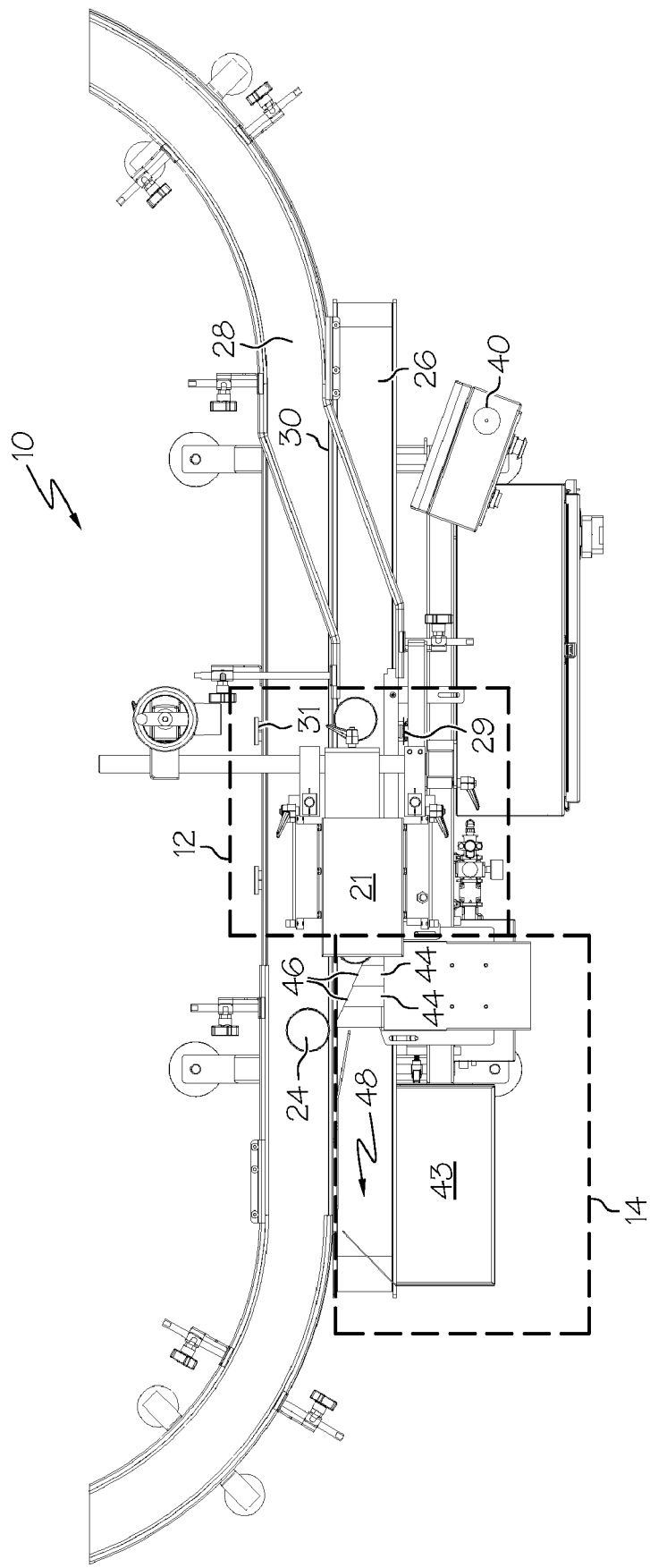
FIG. 1 is a plan view of a foil lid inspection system and controlled divert gate on a conveyor system, in accordance with at least one embodiment of the present invention.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

FIG. 1 depicts a system 10 for detecting and separating defective foil lids on a container in a production line. The system 10 includes a foil lid inspection system, shown generally at 12, and a controlled divert gate, shown generally at 14. The foil lid inspection system 12 is shown in more detail in FIGS. 2A-2B.

Figure 2A:
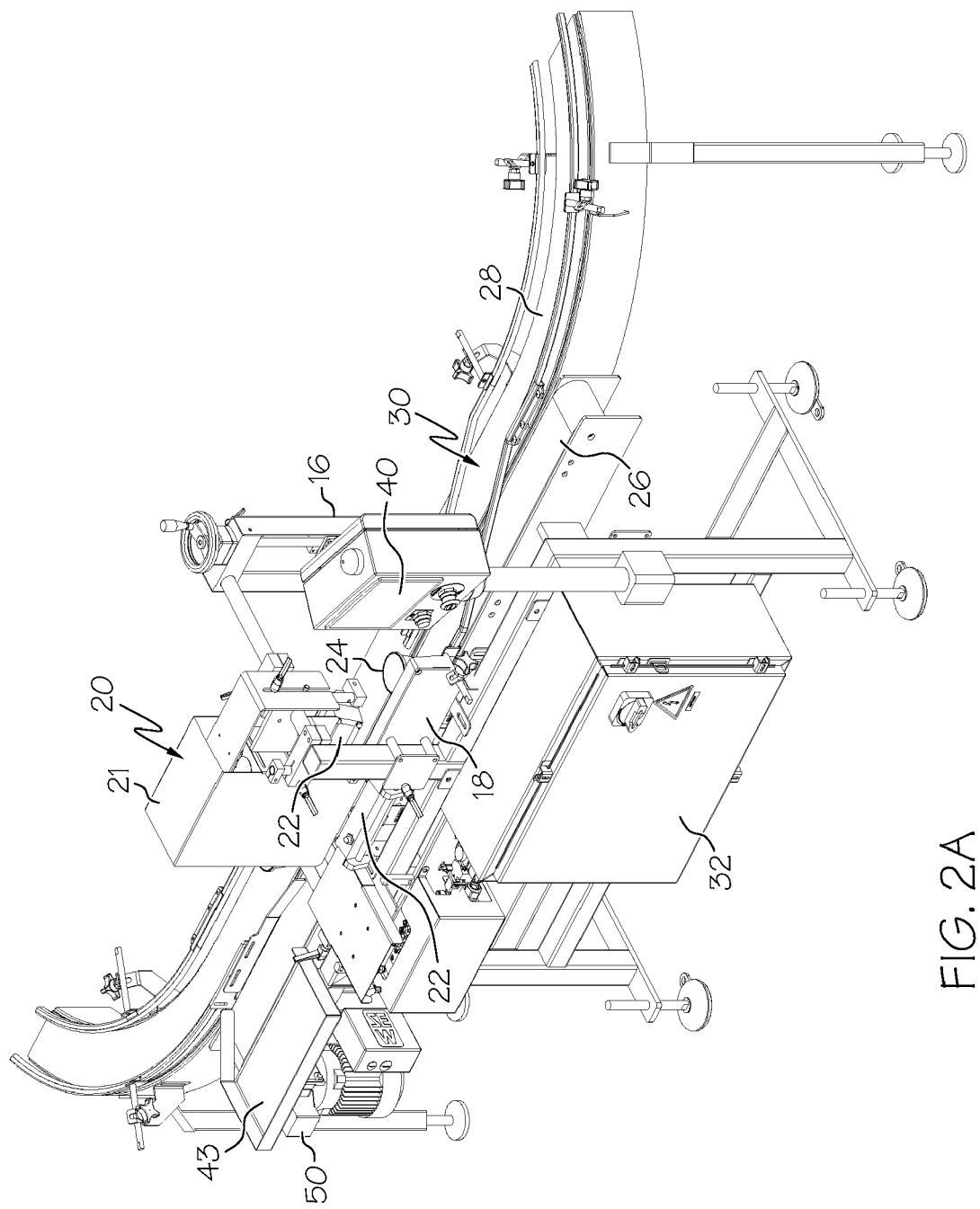
FIG. 2A is a perspective view of the foil lid inspection system and controlled divert gate on a conveyor system of FIG. 1.
Figure 2B:
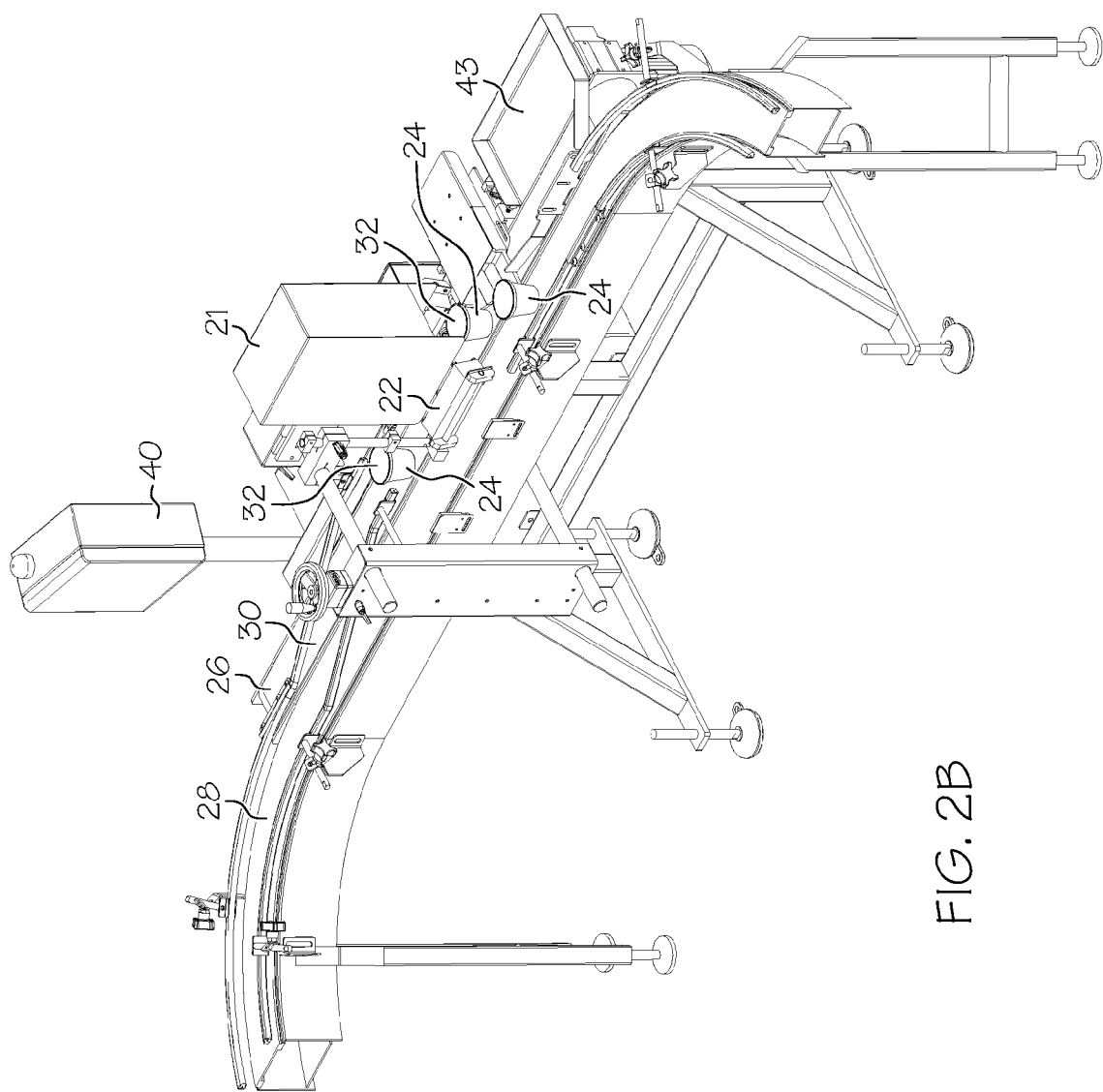
FIG. 2B is another perspective view of the foil lid inspection system and controlled divert gate on a conveyor system of FIG. 1.

Referring now to FIGS. 2A-2B, the foil lid inspection system includes a side view camera 16, side view light source 18, top view camera 20, ambient light cover 21, and top view light source 22. The ambient light cover 21 prevents ambient light from illuminating the top of the foil. Also in at least one embodiment the cover 21 is coated with a low reflective paint in order to keep the lighting source from reflecting onto the top of the foil. Product containers 24 enter the inspection conveyor 26 by side transferring off of the customer conveyor 28 at the side transfer area 30. By running the inspection conveyor 26 faster than the customer conveyor 28, a gap is created between product containers 24.

A product container sensor 29 and reflector 31, as seen in FIG. 1, detect the leading edge of a product container 24. A side view light source illuminates the product container for image capture. In some embodiments, the side view light source remains in an on state while the vision system is in production mode. The sensor further triggers the side view camera image acquisition and programmable logic controller 32 (PLC) position capture.

The side view image of the product container is inspected by inspection software running in the camera. The side view image is a side backlit profile of the container. The side view camera inspection ensures that the lid is present, the lid is not lifted, the container up is upright, and the container is the correct height. The side view image is inspected using a number of set points. For example, the captured image is compared with a trained good image and a pass/fail decision can be made based on the pattern match percentage set point. Also, the system can find a number of edges along the top of the container and determine the pixel distance between the highest and lowest points and compare the distance against the flatness set point. And, the system can determine the width of the container by finding the edges on each side and measuring the width in pixels and comparing against the width set point. And, the system can calculate the angle along the found points on the top of the container and compare against the maximum angle set point. Finally, the highest point found on the top of the container can be compared against the height set point. If the inspection software determines that a product container has failed inspection, the camera inspection system applies a fail signal to an output of the inspection system. The fail signal is applied to an input of the PLC. As will be described in more detail below, the system will then separate the failed product from good product. It should be noted that in most systems, no pass signal is applied to the output, only fail signals.

While a person of ordinary skill in the art will recognize that there are a number of inspection systems that may be used for the purpose described herein, in some embodiments the camera and software are part of the Cognex In-Sight 5100 series inspection system, available from Cognex based in Natick, Mass., USA. Although the Cognex In-Sight 5100 series inspection system includes setup software that allows end users to implement basis inspection tools, in at least one embodiment described herein, the setup software was customized via Cognex's Software Development Kit.

Regardless of whether the product container passes the side view inspection, the product container proceeds through to top view camera inspection. However, only if the product container passed the side view inspection will the top view camera inspection occur. The top view inspection camera is mounted above the conveyor looking straight down at the product container lid. In some embodiments, the product container lid is a foil cover; however one of ordinary skill will recognize that embodiments of the invention can be directed towards a number of other product container lids.

Figure 3:
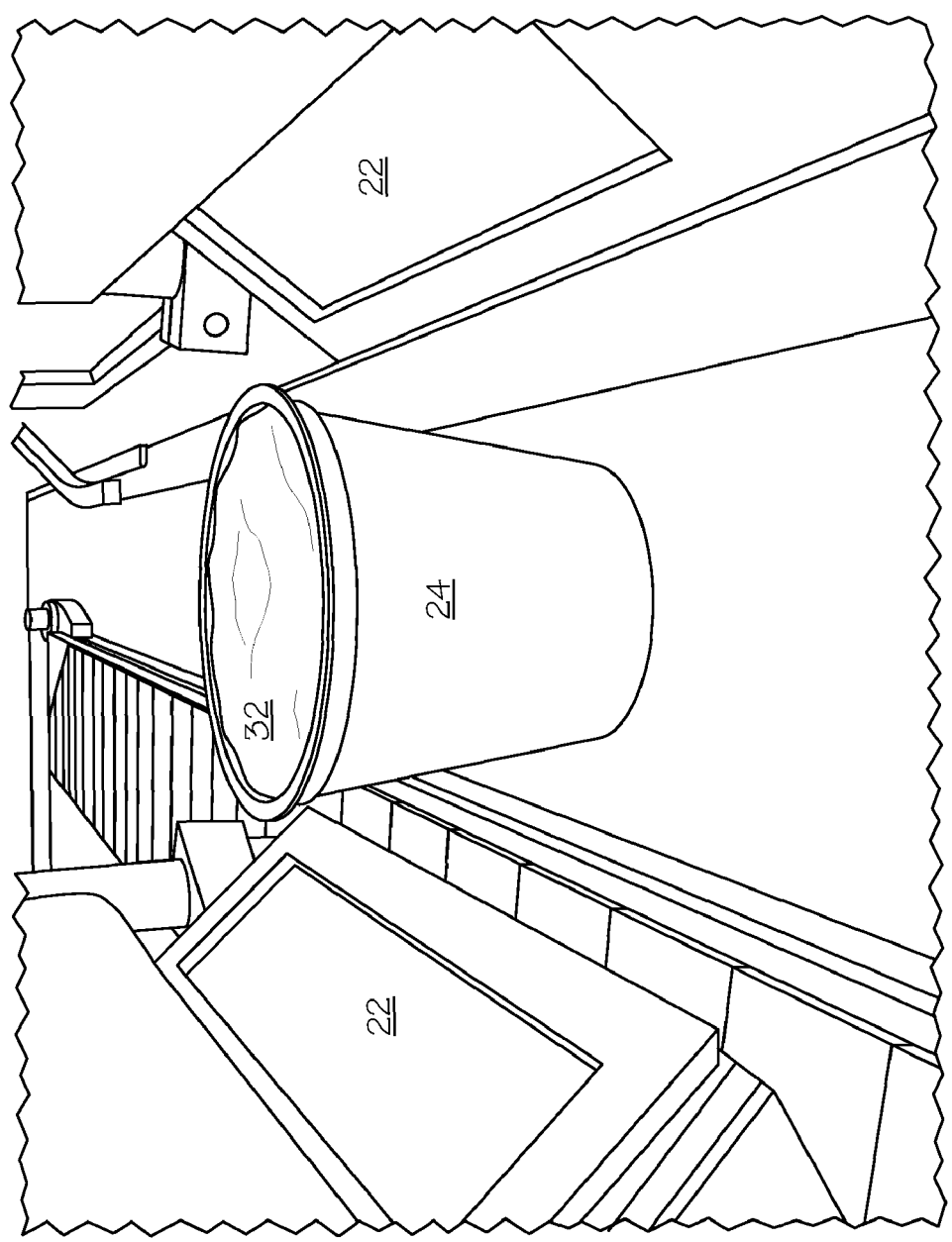
FIG. 3 is an image depicting a product container and light sources in an environment of use, in accordance with at least one embodiment of the present invention.

On each side of the conveyor in the inspection area, there is a high frequency/high intensity light source 22 to the side of the conveyor and angled upwards at the product container, as seen in FIG. 3. Directing light upward at an angle in this manner keeps light off of the conveyor and also off the top of the foil 32, thereby creating sufficient contrast between a white plastic container, for example, and the foil lid and conveyor. Being "angled upwards" means that the light source is positioned to direct light at an angle relative to the surface of the conveyor belt that is neither 0 degrees (horizontal) nor 90 degrees (vertical).

Figure 4B:
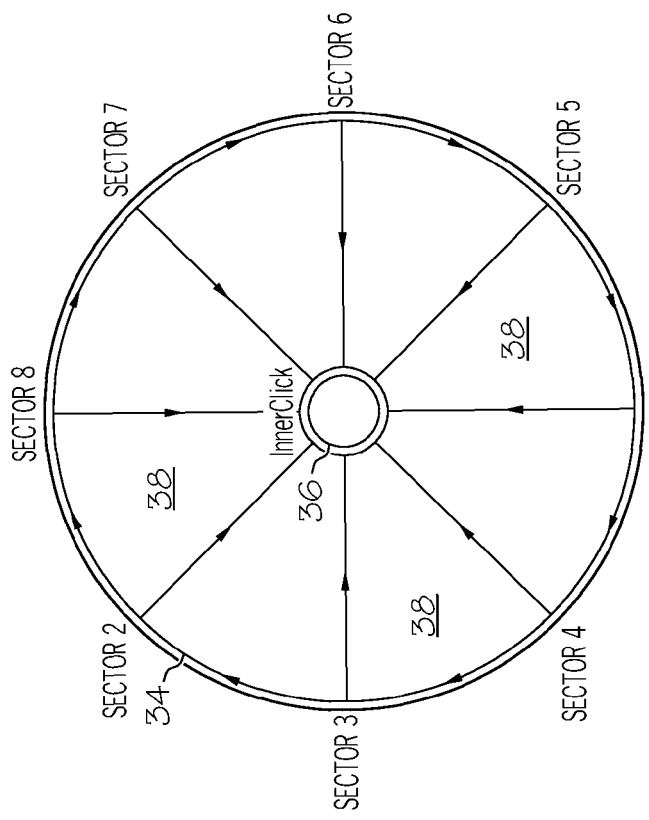
FIGS. 4A-4B is a schematic representation of the overlay onto a product container lid performed by the inspection software, in accordance with at least one embodiment of the present invention.
Figure 4A:
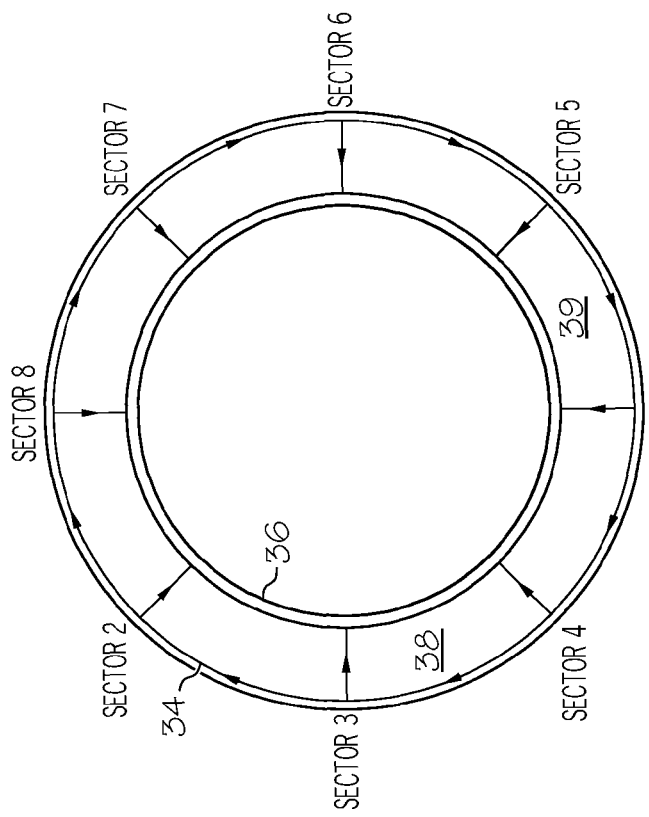

The inspection software used to inspect the foil on a container divides the lid into a plurality of regions and inspects each region. In one embodiment, the product container lid is substantially circular and the inspection software overlays two concentric circles 34, 36 onto the lid, as shown in FIGS. 4A-4B. The outer circle 34 corresponds substantially to the perimeter or edge of the product container. Between the outer circle and the inner circle, the software divides the space, or annulus, between the two concentric circles into a plurality of sectors 38, also shown in FIGS. 4A-4B. The annulus is fully adjustable and in at least one embodiment has eight sectors, as seen in FIGS. 4A-4B. The annulus is fully adjustable in that the outer and inner circles defining the annulus are adjustable, thereby automatically increasing or decreasing the size of the sectors.

As mentioned above, there is a light source pointing at the product container in an upward direction. The inspection system will determine the amount of light, represented by white pixels in the camera image, per sector and in the inner circle. Too many white pixels in one or more sectors, or any white pixels in the inner circle, may indicate a lifted or torn lid. The acceptable amount of white pixels per sector is determined by an operator configured set point. If the amount of white in any given sector exceeds the set point amount, that sector will fail. However, this alone will not result in failure of the product container. The inspection software further includes a set point to control the amount of failed sectors required to fail a container. In contrast to the failure scheme for the sectors, if there are any white pixels detected inside the inner circle, the inspection software will fail the cup regardless of how many failed sectors there are.

Figures 5, 6A:
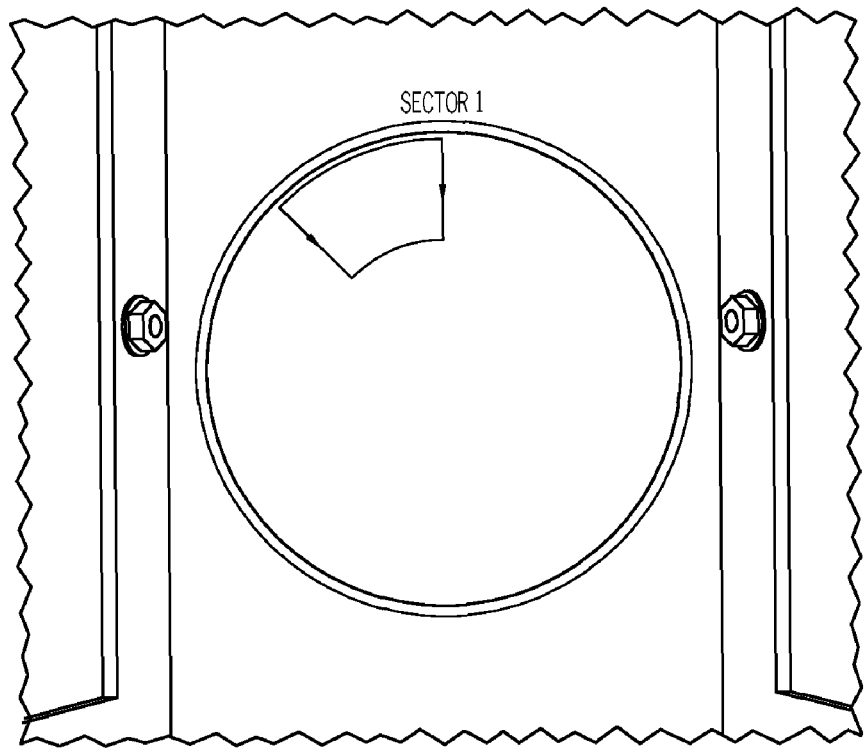
FIG. 5 is a screen image of operator configurable set points for the inspection software, in accordance with at least one embodiment of the present invention.
FIGS. 6A-6B are images depicting product container lids that have failed inspection in accordance with at least one embodiment of the present invention.

An embodiment of an operator configurable settings and results screen is shown in FIG. 5. The line entitled "Amount of White Per Sector %" depicts the results of the current container lid under inspection. In this embodiment, an operator has configured the second line, entitled "Sector %", to have a set point of 20. If the percent of white in any given sector exceeds the set point amount of 20, the sector will fail. However, as mentioned above, this alone will not fail the container. In the third line, the "Sectors" set point is set at 2, and as such, 2 or more failed sectors are required to fail a container. If the percentage of white in any sector exceeds the "Auto Fail %" set point shown in line 5, the inspection software will also fail the cup automatically. The "Threshold" setting at line 4 refers to the value at which each pixel is determined to be white or black based on its grayscale value. Pixels having a value below the threshold value are considered to be black, and pixels having a value above the threshold are considered to be white. The threshold value can be adjusted to eliminate gray readings. Referring again to line 1 of FIG. 5 entitled "Amount of White Per Sector %", in this example the container would be a failure because each of the eight sectors in this embodiment are represented by a value—either 99% or 100%—that is greater than the Sector % set point of 20.

Figure 6B:
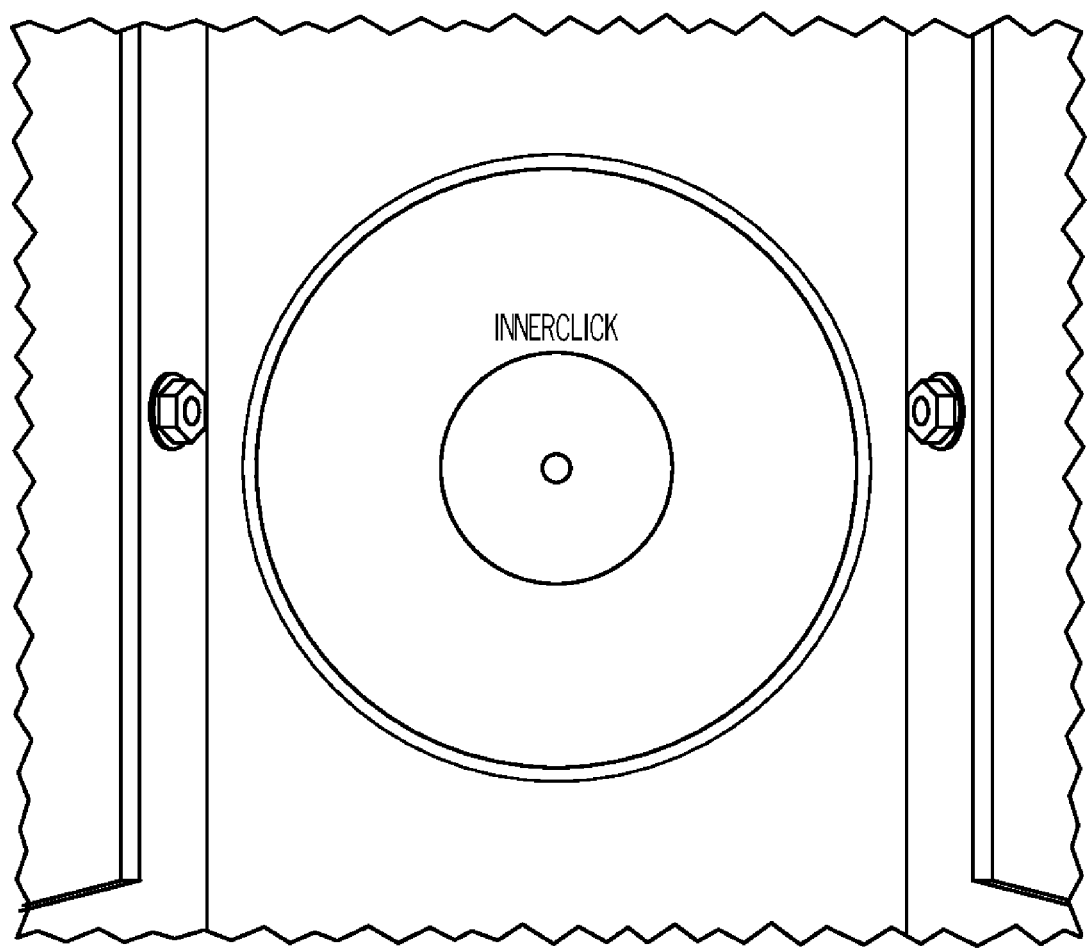

In some embodiments of the present invention, any failures are displayed on a touch screen for an operator to verify. For example, as seen in FIG. 6A, Sector 1 failed because the number of white pixels detected exceeded a maximum threshold, and in FIG. 6B, the inner circle failed because there were white pixels detected. Failed sectors and the inner circle can be highlighted by the system on the touch screen 40, as seen in FIGS. 1-2, to more easily allow verification by the operator. For example, in some embodiments, the boundaries of the failed sector or the inner circle can be highlighted in red.

In some embodiments, the touch screen 40 is a Human Machine Interface (HMI). The HMI is the interface that an operator uses to interact with the inspection system. One embodiment of an HMI is available from Cognex and is sold as a VisionView™ operator interface panel. False failures are often a problem in production lines, and vision systems are no less prone to false failures. False failures are often problematic because there is no means of letting an operator know why the inspection failed on a product that should have passed. The reason the product failed inspection may be unrelated to the product. For example, false failures may be the result of contamination of the lens, the lens being out of focus, lighting failure, and an incorrect product selection to name but a few examples. When a false failure occurs, the operator must alert a technician, engineer, or another individual that has an in-depth knowledge of the vision system, to re-program the system or shut the system off and run it in bypass mode. Obviously, running the vision system in bypass mode defeats the purpose having a vision system checking for quality issues on the production floor.

With an HMI, each failed inspection is available for visual review by an operator. In at least one embodiment, the inspection software used herein has been written to include visual indicators of all possible inspection failures. When a failure occurs, the actual area(s) of failure is highlighted, and an indicator stating what failed is displayed.

Another feature of the HMI is its focus mode. This allows any lens failures such as a dirty lens or mis-adjustments to be corrected right away, thereby reducing downtime. Also, any lighting issues are apparent and can be corrected immediately using the focus mode.

Figure 7:
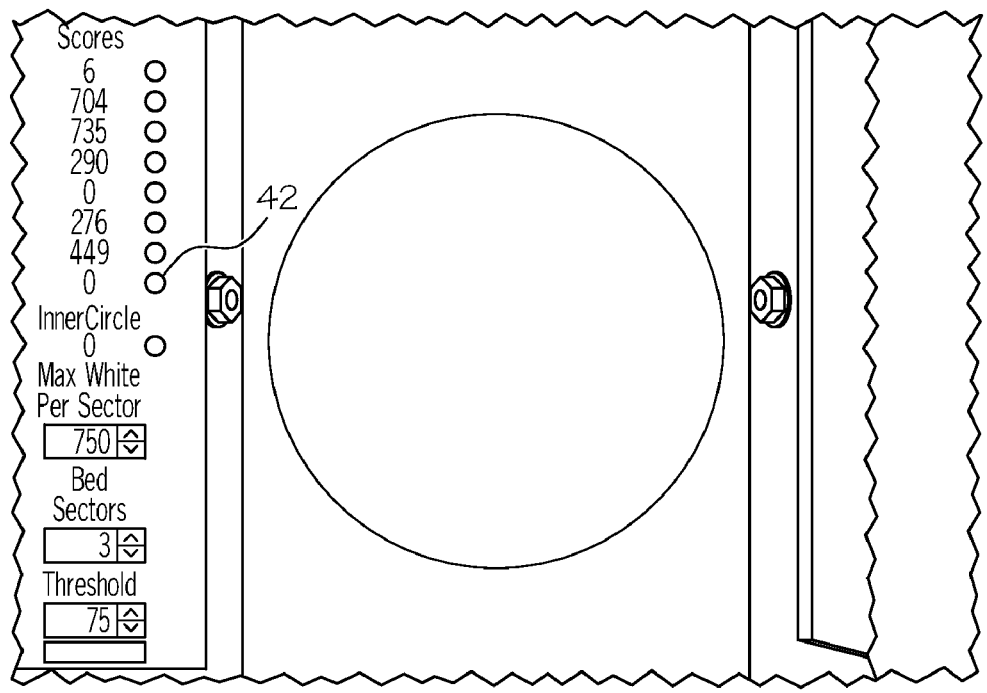
FIG. 7 is an image depicting a passed product container lid and the scores associated with each inspected sector, in accordance with at least one embodiment of the present invention.
Figure 8:
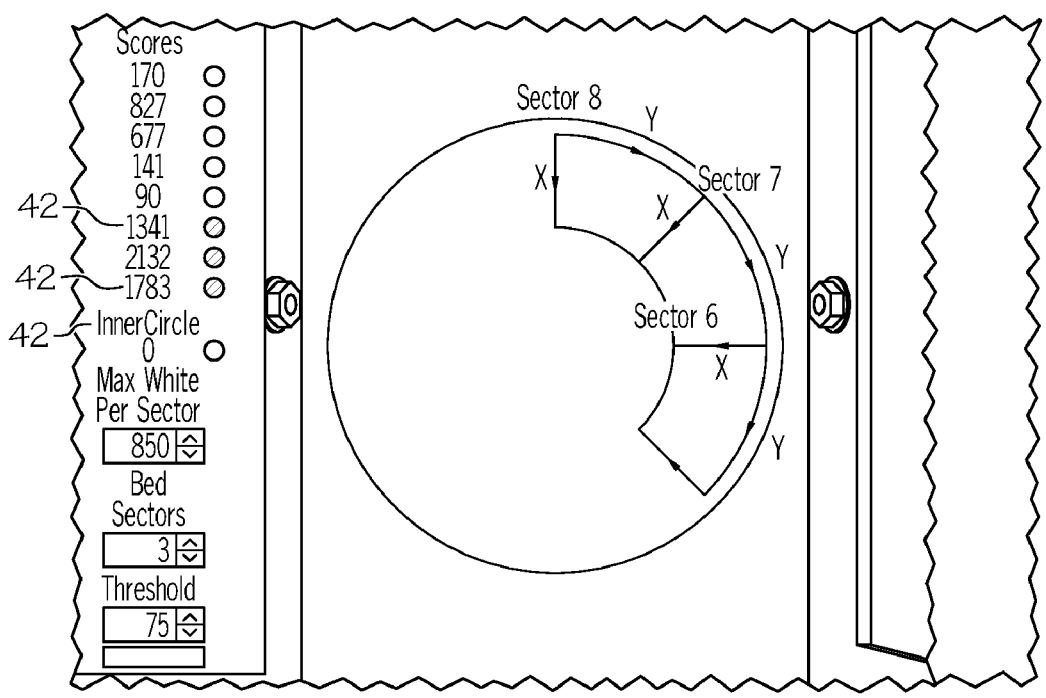
FIG. 8 is an image depicting a failed product container lid and the scores associated with each inspected sector, in accordance with at least one embodiment of the present invention.

Additionally, in at least one embodiment, the system can display the image of the container and the amount of white pixels detected along with a green or red indicator light. For example, in FIG. 7, a passing lid is shown. On the left-hand side of FIG. 7, each of the eight (for the eight sectors) scores, or amount of white pixels detected, is less than the maximum white per sector set point of 750 shown. As such, each sector score can include a color status indicator 42. In this example, all status indicators may be highlighted green to further indicate that each sector is a pass. In the example depicted in FIG. 8, three of the eight sectors failed, as indicated by their score being greater than the maximum white per sector set point of 850 shown. As such, the status identifiers 42 of these three failed sectors may be highlighted red to further indicate failure.

Figure 9:
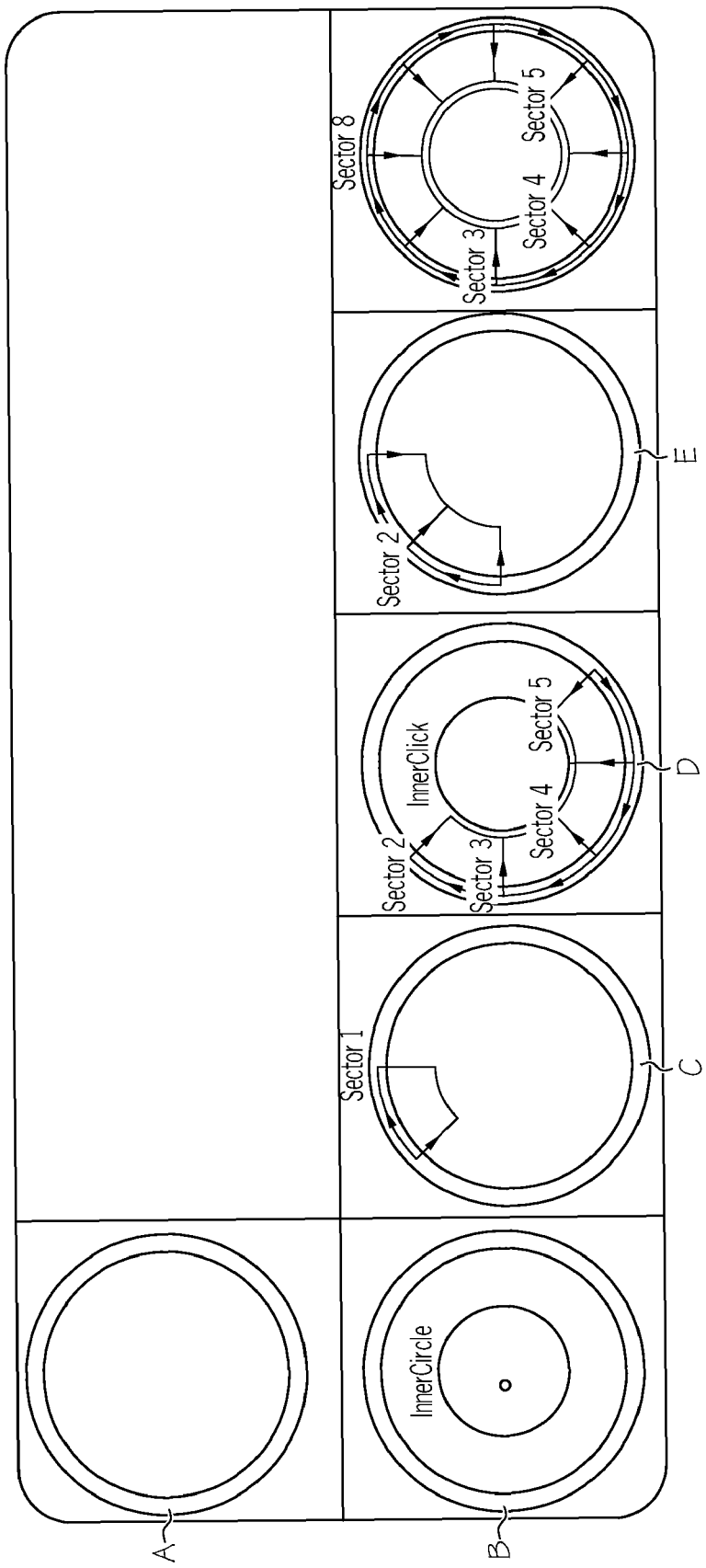
FIG. 9 depicts images of a passed product container lid and failed product container lids, in accordance with at least one embodiment of the present invention.

Turning to FIG. 9, examples of foil lid inspections are depicted. At Frame A, a good lid is shown with no errors. However Frames B-F each depict lids having either multiple failed sectors, a failure in the inner circle, or both.

Figure 10:
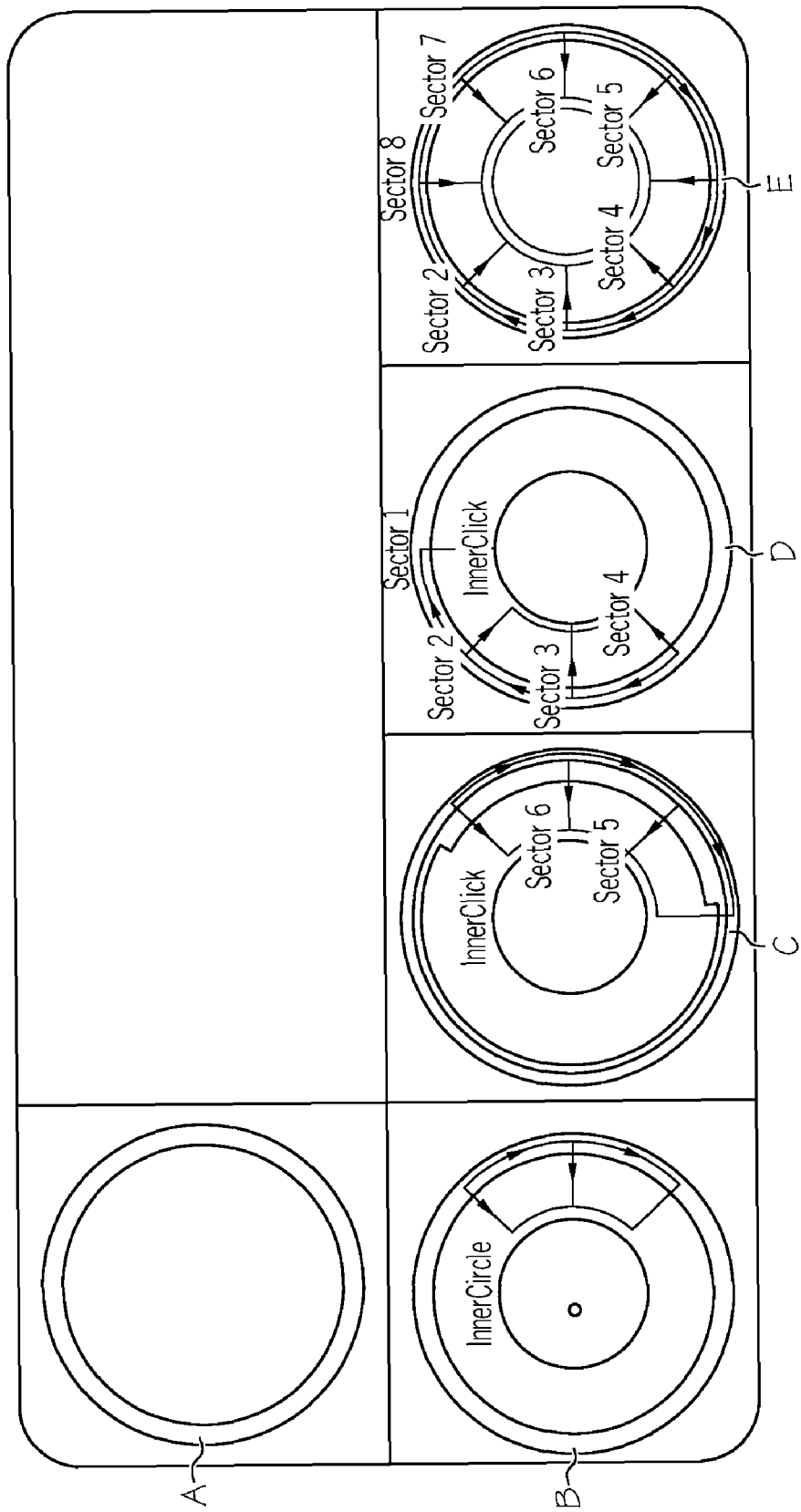
FIG. 10 depicts images of a passed product container lid with an over cap and failed product container lids, in accordance with at least one embodiment of the present invention.

FIG. 10 is similar to FIG. 9, with the exception that these containers include both the foil lid and an over cap to protect the foil. At Frame A, a good lid with an over cap is shown with no errors. However, Frames B-E each depict lids having either multiple failed sectors, a failure in the inner circle, or both, due to misaligned or missing foil lids, for example.

The controlled divert gate will now be described in more detail. Typical divert gates are designed such that passed product moving along a first conveyor are allowed to continue along the first conveyor, while failed products are diverted such that they are not allowed to continue along the first conveyor. Embodiments of the present invention differ from this typical divert gate in that failed products are allowed to continue along the first conveyor into a reject area, while passed products are diverted onto a second conveyor. With respect to the embodiment depicted in FIGS. 1-2, the first conveyor is the inspection conveyor 28, the second conveyor is the customer conveyor 26, and the reject area is shown at 43. In at least one embodiment, as mentioned above, failed product containers 24 are generally those containers having defective lids. It is often desirable to allow products that are not sealed properly to continue along their original trajectory rather than exert a force to divert them and risk tipping over the container and contaminating the machine. As seen in FIG. 1, the reject fingers 44 are positioned such that collectively their angled product container contacting surfaces 46 (that is, angled relative to the direction of motion 48 along the inspection conveyor 26) gently divert passed product containers 24 from the inspection conveyor 26 back onto the customer conveyor 28. As seen in FIG. 2B, the passed containers 24 are being diverted onto the customer conveyor 28, and away from the reject area 43.

Figure 11:
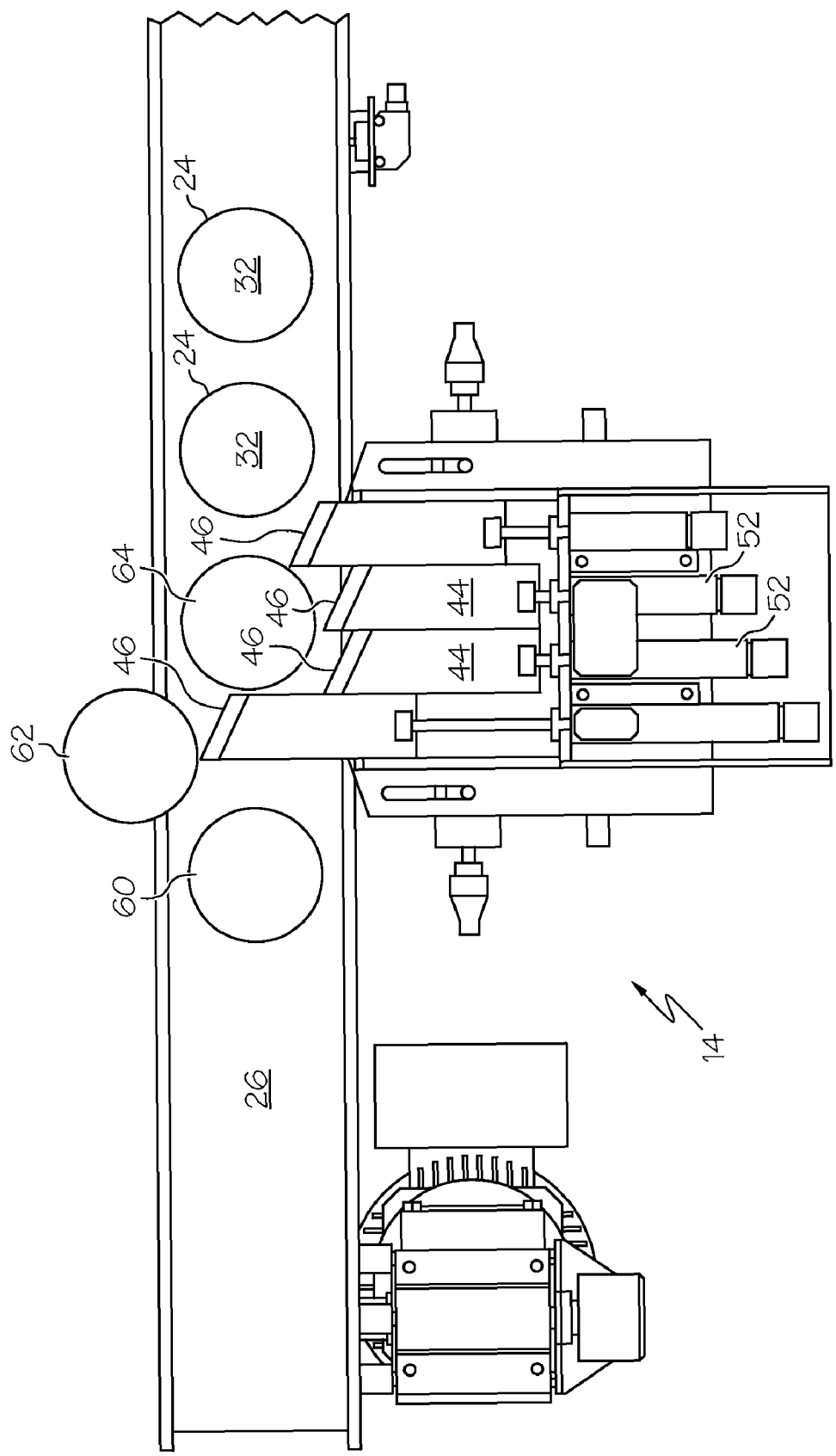
FIG. 11 is a plan view of a controlled divert gate with reject fingers, in accordance with at least one embodiment of the present invention.

The divert gate 14 having reject fingers 44 is shown in detail in FIG. 11. The conveyor 26 transporting the product 24 is mechanically connected to an encoder 50 (shown in FIG. 2A). An encoder output is applied to a PLC input so that position and speed of the inspection conveyor 26 are calculated and monitored in real time. Each reject finger 44 is engaged to a cylinder 52 that is actuated by a pneumatic solenoid (not shown) that is wired to the PLC outputs. While the divert gate shown has four reject fingers, other embodiments may include more or less than four reject fingers. In the depiction shown in FIG. 11, product container 60 has failed inspection and is proceeding to the reject area, product container 62 passed inspection and was diverted off of the inspection conveyor 26, and product container 64 failed inspection and the reject fingers are in the process of retracting in order to allow it to reach the reject area.

Detailed operation of the divert gate will be described immediately following this general description. When the PLC outputs a fail signal, the reject signal is first applied to a first solenoid (not shown) which actuates a first cylinder to retract a first finger. Next, a second solenoid (not shown)

actuates a second cylinder to retract a second finger. This sequence continues until all of the fingers have been retracted, thereby allowing the rejected container to move along the conveyor to the reject area. The operation of the fingers is designed such that once the rejected container has moved beyond the retracted first finger, for example, the first finger would be moved back into its pass state if and when the next container is a pass. Therefore if two failed containers pass by, the fingers will remain in the fail positions. It should be noted that in some embodiments, the leading edge of a container passing by each finger will change that finger's state only.

When a product sensor detects a container's leading edge, the PLC logs its capture position. Each time a capture position is logged, logic is triggered that calculates the conveyor's position at which the leading edge of the logged container will reach each reject finger in the divert gate system. The actual distance from the product sensor location to each reject finger is added to the calculated reaction times for each finger. These reaction times are based on the measured time to move the finger from the pass position to the reject position and from the reject position to the pass position. Based on the conveyor speed, these reaction times are then used to determine how much distance is needed to anticipate the triggering of each valve to the desired pass/reject position.

Additionally, the divert gate system also compensates for any slip that occurs between the belt and a passed product container when it is diverted. This is accomplished by calculating a virtual position for each finger in the pass position, adding the measured slip distance that occurs at each finger, and applying this slip distance as an offset to the next finger. These capture positions are then stored in a ring counter variable array which will accumulate and roll through capture positions as encountered. Individual logic for each finger monitors the current index in the ring variable array for the conveyor to reach the next reject position, and then based on the pass/reject status, the logic sets the state of the finger to correspond to the pass/reject status. After each capture position is applied to the finger, the ring counter index is incremented to the next array position to start monitoring for the next capture. If the ring counter index is greater than the maximum array index, the ring counter index is looped back to the first variable array position. This method allows multiple rejects to be tracked between the capture sensor and the reject device. The ring counter variable size is only limited by the amount of memory installed in the PLC. For example purposes only, assume that the capture position of the container is 1000, the first reject finger (the shortest finger shown in FIG. 1) is at a position of 500 away from the container's capture position, and that the reaction time of the first reject finger corresponds to a distance of 10. The first finger would have a value of 1000+500−10, or 1490. Regarding the second finger, assume that it was at position of 600 away from the container's capture position, and that the reaction time of the second reject finger corresponds to a distance of 20 (it would be longer than the first finger because the second finger must travel further). The second finger would have a value of 1000+600−20, or 1580. However, a slip amount needs to be added to this value because a passed container will be diverted. Assume that the value of the slip is 100, and then the value would be 1580+100, or 1680.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

This completes the description of the preferred and alternate embodiments of the invention. Those skilled in the art may recognize other equivalents to the specific embodiment described herein which equivalents are intended to be encompassed by the claims attached hereto.

What is claimed is:

1. A foil lid inspection system for detecting and separating defective foil lids on a container in a production line, the system comprising:
   at least one light source for illuminating the container, the at least one light source positioned to direct light in an upward direction at the container;
   an inspection camera disposed above the foil lid, the camera comprising at least one output; and
   inspection software in communication with the inspection camera, the inspection software being constructed and arranged to determine if the foil lid on the container is defective,
   wherein a reject signal is applied to the at least one output if the software determines that the foil lid is defective, the software is constructed and arranged to overlay two concentric circles on a foil lid, the two concentric circles defining a space therebetween, the software further constructed and arranged to divide the space into a plurality of sectors, measure the amount of white pixels in each of the plurality of sectors, and compare the measured amount of white pixels in each of the plurality of sectors against a first operator configurable set point in order to determine whether each of the plurality of sectors is a pass sector or a fail sector.

2. The system of claim 1, wherein the software is further constructed and arranged to compare the number of fail sectors against a second operator configurable set point of maximum fail sectors to determine if the reject signal or the pass signal should be applied to the at least one output.

3. The system of claim 2, wherein the two concentric circles comprise an outer circle and an inner circle, and wherein the reject signal is applied to the at least one output if any white pixels are measured within the inner circle.

4. The system of claim 3, wherein the software is further constructed and arranged to include a third operator configurable set point such that if the measured amount of white pixels in any of the plurality of sectors exceeds the third operator configurable set point the reject signal is applied to the at least one output.

5. The system of claim 4 in combination with a controlled divert gate, the gate comprising:
   a plurality of fingers;
   a plurality of cylinders; and
   a plurality of pneumatic solenoids,
      wherein each of the plurality fingers is engaged to a cylinder, and each cylinder is in communication with a solenoid, and
      wherein each solenoid is in electrical communication with an output of a programmable logic controller.

6. The system of claim 5, each of the plurality of fingers comprising a product container contacting surface, wherein when in an extended position, the plurality of contacting surfaces form an angle relative to a direction of motion along a first conveyor.

7. The system of claim 6, wherein when the programmable logic controller calculates a pass state the plurality of fingers are in an extended position and when the programmable logic controller calculates a reject state the plurality of fingers are in a retracted position.

* * * * *